United States Patent [19]

Burton et al.

[11] 4,407,278
[45] Oct. 4, 1983

[54] PENILE PROSTHESIS WITH IMPROVED FLUID CONTROL

[75] Inventors: John H. Burton; Bradford G. Staehle, both of Minnetonka; Charles C. Kuyava, Brooklyn Center, all of Minn.

[73] Assignee: American Medical Systems, Inc., Minnetonka, Minn.

[21] Appl. No.: 373,481

[22] Filed: May 3, 1982

Related U.S. Application Data

[63] Continuation-in-part of Ser. No. 264,202, May 15, 1981, Pat. No. 4,383,525.

[51] Int. Cl.³ .............................................. A61F 5/00
[52] U.S. Cl. .................................................... 128/79
[58] Field of Search ................................. 128/79; 3/1

[56] References Cited

U.S. PATENT DOCUMENTS

| | | | |
|---|---|---|---|
| 3,853,122 | 12/1974 | Strauch et al. | 128/79 |
| 4,009,711 | 3/1977 | Uson | 128/79 |
| 4,201,202 | 5/1980 | Finney et al. | 128/79 |
| 4,353,360 | 10/1982 | Finney et al. | 128/79 |

Primary Examiner—John D. Yasko
Attorney, Agent, or Firm—Williamson, Bains, Moore & Hansen

[57] ABSTRACT

A surgically implantable prosthesis for the treatment of penile erectile impotence in male patients. The device comprises at least one elongated cylinder implanted within one of the corpora cavernosa of the penis. The flexible, distal end of the cylinder is adapted to rigidize upon being filled with pressurizing fluid. The rear tip or proximal end of the cylinder is formed to provide a chamber which serves as a fluid reservoir. Valve means contained within the flexible, distal end section of the cylinder, for conveniently accessible manual manipulation is utilized to selectively control fluid flow between the rear tip reservoir and the distal end of the cylinder. The prosthesis further includes a manually operable pump means utilized to transfer pressurized fluid from the rear tip reservoir to the distal end of the cylinder in order to achieve an erection. The walls of the rear tip reservoir itself may serve as the pump means, or a separate pump may be implanted within the scrotum.

21 Claims, 22 Drawing Figures

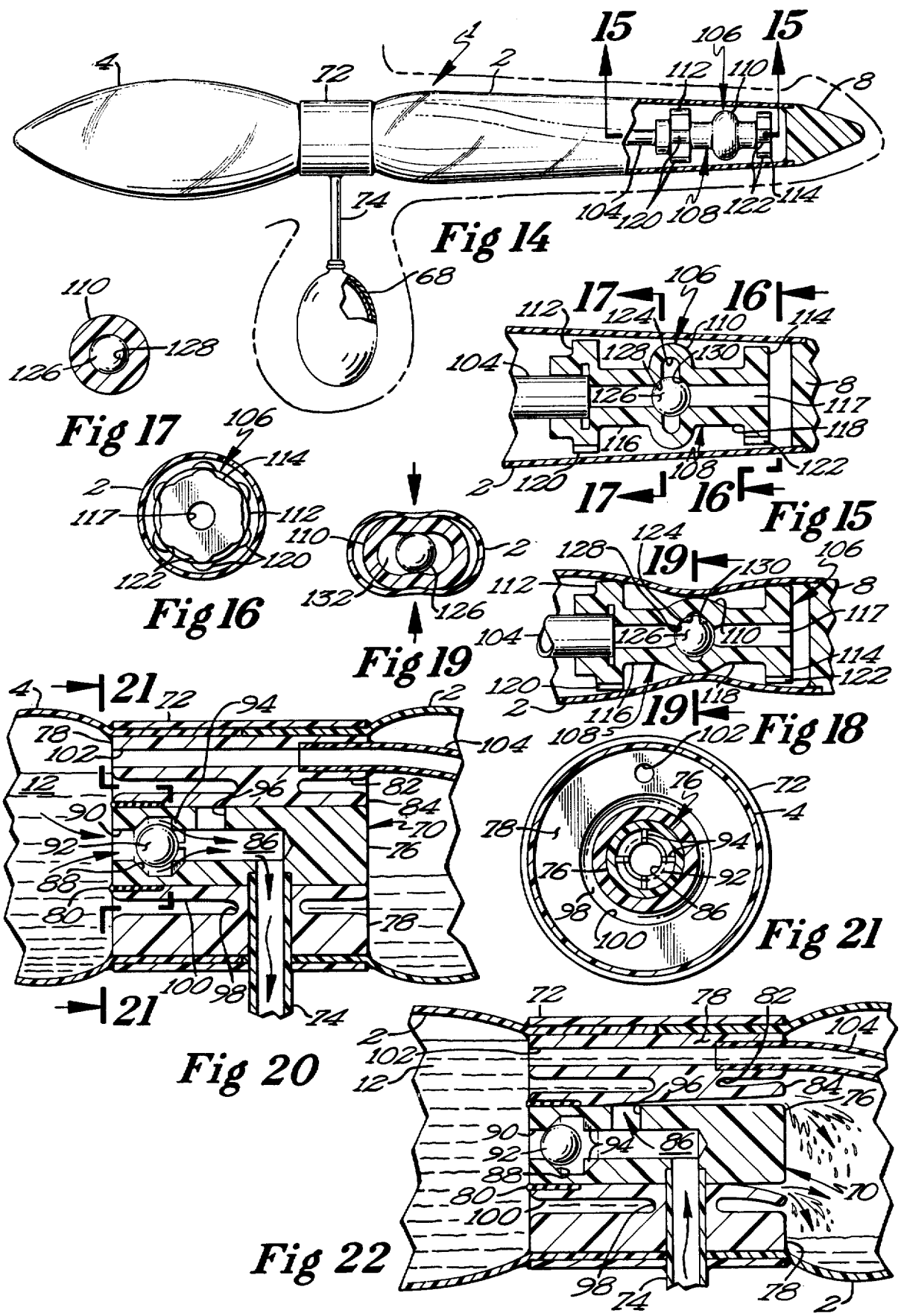

PENILE PROSTHESIS WITH IMPROVED FLUID CONTROL

BACKGROUND OF THE INVENTION

This is a continuation-in-part of the U.S. Application No. 264,202 filed May 15, 1981, now U.S. Pat. No. 4,383,525 and entitled IMPLANTABLE PENILE PROSTHETIC CYLINDER WITH INCLUSIVE FLUID RESERVOIR. This invention relates generally to the field of implantable medical prosthetic devices for treating male erectile impotence, and more particularly to penile prosthetic implants operated by fluid pressure supplied from an implanted pump device.

Implantable penile prostheses for the management of erectile impotence utilizing inflatable cylinders which are implanted within the penis are described and disclosed by Scott et al in *Urology*, Vol. II, No. 1, July 1973, pp. 80-82, and by Kothari et al in the *Journal of Biomechanics*, Vol. V, 1972, pp. 567-570. The prosthetic devices disclosed in those articles comprise a reservoir to hold a radiopaque fluid used to activate the device through inflatable cylinders adapted to be placed inside the corpora cavernosa of the penis, and two pumping mechanisms for inflating and deflating the cylinders. The inflatable cylinders are disclosed as comprising collapsible tubes constructed of dacron reinforced silicone rubber and having a shape simulating the corpora cavernosa. Valves are employed in the disclosed fluidic system in such a way as to permit selective actuation of the pumping mechanisms to inflate and deflate the cylinders. In this manner the patient is able to selectively produce an erection and to return the penis to a flaccid state by manual manipulation of the pumping mechanisms.

A method and device for achieving a penile erection is described by Strauch et al in U.S. Pat. No. 3,853,122. That patent discloses an elongated, flexible, and stretchable hollow tube implanted in the penis. A flexible, fluid container is provided for implantation in the scrotum or in the lower abdomen of the patient. Pressing on the implanted container serves to displace the fluid into the tube to render the tube relatively rigid, thus providing the desired erection.

Another penile prosthesis for the management of erectile impotence is described by Uson in U.S. Pat. No. 4,009,711. Uson shows a body member having a nondistensible portion and a distensible body portion, with the latter being connected by a suitable conduit means to a fluid supply source implanted within the patient. The nondistensible portion is preferably made of plastic material, such as Silastic, which is relatively rigid and is adapted to be implanted into the root end of the corpus cavernosum of the penis to anchor the prosthetic device in place. The distensible body portion is connected by fluid conduit means to a pump bulb implanted within the scrotum. The Uson prosthesis is thus rigid at the root of the penis, and inflatable at the pendulous portion of the penis.

The penile erection system disclosed by Buuck in U.S. Pat. No. 3,954,102 is an improved variation of that disclosed in the aforesaid Scott et al and Kothari et al articles. The Buuck patent discloses a pair of inflatable and collapsible cylinders adapted to be implanted within the corpora cavernosa of the penis to simulate their function. Each cylinder includes a cylindrical silicone rubber body or sleeve which is expansible circumferentially and also longitudinally. A single pump bulb implanted within the scrotum is utilized to selectively deliver fluid to the inflatable cylinders through a valve system. A separate, fluid reservoir implanted within the abdomen of the male patient contains the fluid utilized to activate the inflatable cylinders. Pumping of the squeeze bulb within the scrotum serves to transfer fluid from the reservoir to the cylinders. A manually actuable bypass valve contained within the pump bulb implanted within the scrotum is manipulated to permit pressurized fluid to flow from the cylinders back to the fluid reservoir in order to return the penis to a flaccid state.

Prior art inflatable penile prostheses as implanted and used in actual practice have required relatively large fluid reservoirs as disclosed in the Buuck patent to contain the amount of fluid necessary to inflate elongated, stretchable hollow tubes implanted in the penis. It is disadvantageous to implant a large fluid reservoir in the scrotum. It is also undesirable to implant separate structures, such as a fluid reservoir and connecting fluid conduits, at remote locations from the penis or from a pump device implanted in the scrotum. Such fluidic systems complicate the surgical implant procedure. One approach to simplifying the implantable prosthesis, particularly with respect to the fluid pressurizing system, is disclosed in U.S. Pat. No. 4,267,829, of which the aforesaid Application No. 264,202 is a continuation-in-part. In that patent, there is disclosed a pressurizable implant cylinder which is comprised of a substantially rigid front or distal portion, a rigid rear portion for mounting inside the root end of the penis, and a tubular section attached to and mounted between the front and rear portions so as to define a chamber which is connected to pump means. The tubular section is collapsible but resists stretching so that the volume of the chamber undergoes only a small change as the penis is caused to go between a nonerect, bent condition and an erect condition. Therefore, only a small volume of fluid is required to actuate the cylinder to an erect, rigid condition. The pump means as disclosed in the aforesaid U.S. Pat. No. 4,267,829 may take the form of a separate pump bulb implanted within the scrotum or a fluid chamber formed within the distal end of the implantable cylinder to provide a fully self-contained implantable prosthesis.

The implantable penile prosthesis of the aforesaid Application No. 264,202 reflects a further improvement and variation of a fluid pressurized prosthetic device with a simplified fluidic system which does not require a separate fluid reservoir implanted in the abdomen or other remote location. The implantable penile cylinder is disclosed as having a fluid pressurizable distal end section and a proximal or root end section having a self-contained fluid reservoir chamber formed therein. A valve mechanism positioned within the cylinder is constructed to open under the pressure generated by a pumping device utilized to transfer fluid from the rear or root end reservoir chamber to the expansible distal end for achieving an erectile state. Manual manipulation of the valve is required to return fluid from the distal end of the implant cylinder to the reservoir chamber in the proximal end thereof.

There are two potential problems associated with the built-in, root or rear end reservoir arrangement of U.S. Application No. 264,202. One relates to the possible need for critical surgical placement of the implant cylinders for proper valve location and resulting manual accessibility. The other arises from the risk of an inadvertent erection which could be caused by pressure generated by sitting on the reservoir chamber in the proximal, root end of the implant cylinder. The improved penile prosthesis disclosed herein embraces features designed to overcome such possible difficulties.

BRIEF SUMMARY OF THE INVENTION

This invention is directed to an implantable penile prosthesis of the fluid operated type. A flexible, fluid pressurizable, cylinder adapted to be implanted within the corpus cavernosum along the distal end of the penis is combined with a fluid reservoir, pump means and control valve in a compact fluidics arrangement which greatly simplifies the implant surgery required and reduces associated risk and patient discomfort.

A further object is to provide such a simplified penile prosthesis for treatment of male impotence which permits the patient to readily manipulate the pump and control valve to selectively produce an erection or maintain the penis in a nonerect, flaccid state.

This invention also has as an objective the provision of an implantable penile prosthesis which may be implanted, in part, in the scrotum but which does not occupy so much of the intrascrotal space as to interfere with the functioning of bodily organs contained therein or cause patient discomfort.

It is a further object to provide an implantable penile prosthesis of the aforesaid type which does not require the surgical implantation of components of the fluidics system at locations remote from the penis.

These basic objectives are realized by an implantable penile prosthesis comprised of an elongated cylinder adapted to be preferably implanted within the corpus cavernosum of the penis, with the cylinder including a fluid pressurizable distal end section and a self-contained fluid reservoir chamber formed within one end thereof. A valve mechanism for controlling the flow of fluid back and forth between the reservoir chamber and the distal end of the cylinder is also contained within the cylinder. The prosthesis further comprises pump means manually operable to transfer fluid under pressure from the reservoir chamber to the distal end of the cylinder implanted within the distal or pendulous end of the penis for producing an erection.

Preferably, the proximal, rear or root end section of the cylinder is formed to provide the fluid reservoir chamber. In one preferred embodiment, the reservoir chamber within the implant cylinder also serves as the pump means. The walls of the rear end section of the cylinder forming the fluid reservoir are resiliently compressible; and, upon implantation, are accessible for direct manual pumping action through the patient's perineal tissue. The aforesaid valve mechanism is preferably positioned within the distal end of the implant cylinder so that upon implantation it will be located within the pendulous penis where it will be readily locatable and accessible for manual actuation. A fluid conduit within the implant cylinder carries fluid back and forth between the rear reservoir chamber and the valve.

In a particularly advantageous form of the invention, the control valve is constructed as a double check valve, normally blocking flow in both directions between the fluid reservoir chamber and the inflatable distal end section of the implantable cylinder. External manipulation in the form of squeezing pressure applied manually to the pendulous penis is required to unseat the valve for both inflation and deflation. This valve construction precludes inadvertent pressurization of the distal end of the implant cylinder, and an undesired erection, as might occur by sitting on the proximal end reservoir chamber.

In an alternative version of the prosthesis, the pump means comprises an elastomeric bulb adapted to be implanted within the scrotum. The pump bulb is in fluid flow communication with the aforesaid reservoir chamber and distal end section of the implant cylinder through a valve assembly contained within the cylinder. The valve assembly comprises flow check devices which function to permit fluid flow from the reservoir chamber to the distal end section of the cylinder only when the pump is actuated through the scrotal skin. A fluid conduit extending within the implant cylinder serves to return fluid to the reservoir chamber in the proximal end of the implant cylinder when deflation is desired. A double check valve as described above normally blocks flow in both directions through the fluid conduit, and must be manually actuated to obtain return flow for deflation. Thus, fluid is locked in the proximal, rear reservoir chamber of the implant cylinder, so as to preserve the volume of fluid required for inflation of the distal end and to prevent inadvertent pressurization thereof.

These and other objects and advantages of the invention will be readily understood as the following description is read in conjunction with the accompanying drawings wherein like reference numerals have been used to designate like elements throughout the several views.

BRIEF DESCRIPTION OF THE DRAWINGS

FIG. 14 is a side elevation view showing an alternative embodiment of the penile prosthesis as implanted in a male patient with a separate scrotal pump, with the prosthesis in an erect condition;

FIG. 15 is a fragmentary, section view taken along lines 15—15 of FIG. 14 and showing a preferred embodiment of the double check valve structure in the distal end of the penile prosthesis;

FIG. 16 is a section view taken along lines 16—16 of FIG. 15 and showing an end view of the valve assembly;

FIG. 17 is a section view through the check valve element of the valve assembly in its closed position, taken along lines 17—17 of FIG. 15;

FIG. 18 is a fragmentary, section view taken at the same location on FIG. 14 as is FIG. 15, but with the valve manually displaced to an open position for return fluid flow to the reservoir chamber;

FIG. 19 is a section view through the check valve element in its open position, taken along lines 19—19 of FIG. 18;

FIG. 20 is a fragmentary, section view showing on an enlarged scale the valve assembly and interconnecting portions of the penile prosthesis cylinder of FIG. 14, the check valve being shown in its position on the pump suction stroke;

FIG. 21 is a vertical section view of the valve assembly taken along lines 21—21 of FIG. 20; and FIG. 22 is a fragmentary, section view of the same valve assembly shown in FIG. 20, but with the valve elements shown in the pumping stroke position.

DESCRIPTION OF THE PREFERRED EMBODIMENT

Figure 1:
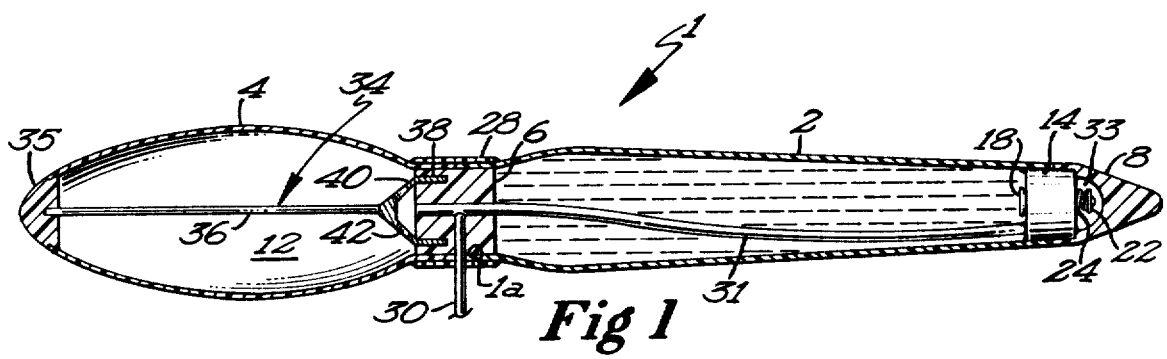
FIG. 1 is a top, plan view of one preferred embodiment of the penile prosthesis of this invention.

Referring now to the drawings, there is shown in FIGS. 1 through 5 one preferred embodiment of the implantable penile prosthesis. The prosthesis is comprised of an elongated cylinder generally indicated by reference numeral 1. Cylinder 1 is adapted to be implanted within the patient's penis, and preferably within one of the corpus cavernosum of the penis. Cylinder 1 is comprised of a distal end section 2 and a proximal or root end section 4 separated by a connecting block section generally indicated by reference numeral 6. Distal end section 2 is flexible and is adapted for implantation within the pendulous segment of the penis. To that end, distal section 2 is tapered along its length from a point adjacent its end near section 6 towards its distal tip. This shape conforms generally to the tapered shape of the corpora cavernosa of the penis. More sharply tapered tip 8 is adapted to be positioned under the glans 10 of the penis as shown in FIG. 6. Thus, though the tubular prosthetic insert 1 is generally referred to as a cylinder, it is to be understood that the distal end section 2 of the cylinder is preferably tapered as described herein.

Distal end section 2 is formed from a medical grade, biocompatible material, preferably polyurethane, which will permit it to flex and bend, whereby the penis may assume a bent, nonerect condition as shown in FIG. 6; however, the construction of distal section 2 is such that it will be impervious to fluid, and will expand and rigidize upon being filled with a pressurizing fluid so as to permit the penis to assume an erect state. The extent to which distal end section 2 actually expands in girth and length under fluid pressure depends upon the particular materials from which it is constructed.

Figures 2, 3:
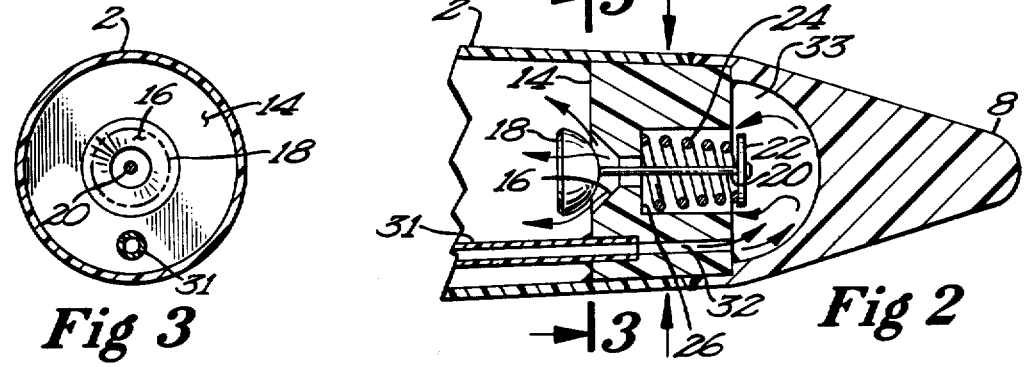
FIG. 2 is a fragmentary, section view showing on an enlarged scale the valve assembly and interconnecting portions of the penile prosthesis cylinder of FIG. 1.
FIG. 3 is a section view of the valve mechanism of FIG. 1 taken along lines 3—3 of FIG. 2.

As may be noted most clearly by reference to FIGS. 1 and 2, distal section 2 and proximal section 4 of the implant device 1 are preferably formed from the same material joined together within section 6 at a sealed joint, as by gluing, to form a continuous tubular implant device 1. Proximal, root section 4 of the implant device is formed to provide a fluid reservoir chamber indicated by reference numeral 12 in FIGS. 1 and 6. Thus, in this manner, the reservoir chamber for pressurizing fluid is self-contained within the body of generally cylindrical prosthetic implant device 1. When implanted within a male patient as shown in FIG. 6, proximal reservoir chamber section 4 of the implant 1 will be positioned in the root segment of a corpus cavernosum. This location ensures the accessibility of reservoir chamber proximal section 4 for manual manipulation when it also serves as a pump as hereinafter set forth.

Figures 4, 5:
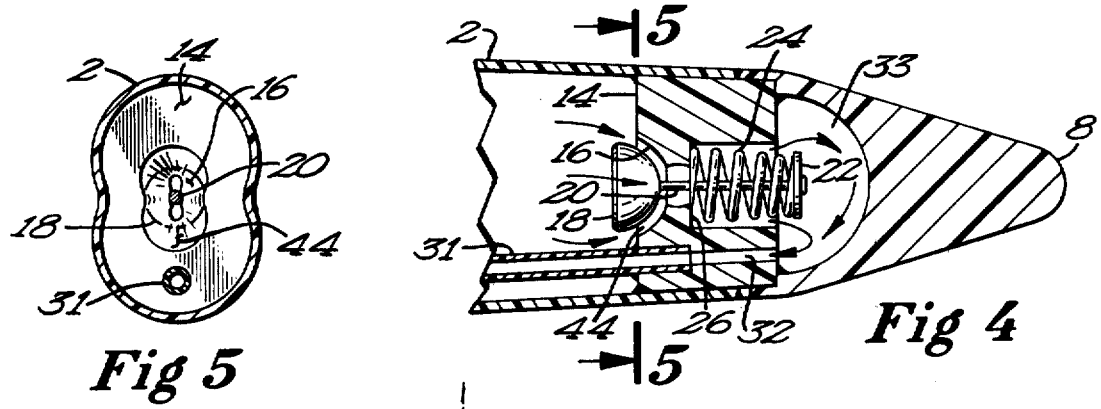
FIG. 4 is a fragmentary view of the valve assembly like FIG. 2, but showing the valve in the open actuated position for return flow and deflation.
FIG. 5 is a section view of the valve mechanism taken along lines 5—5 of FIG. 4 and showing the valve seat displaced to open the valve.
Figure 6:
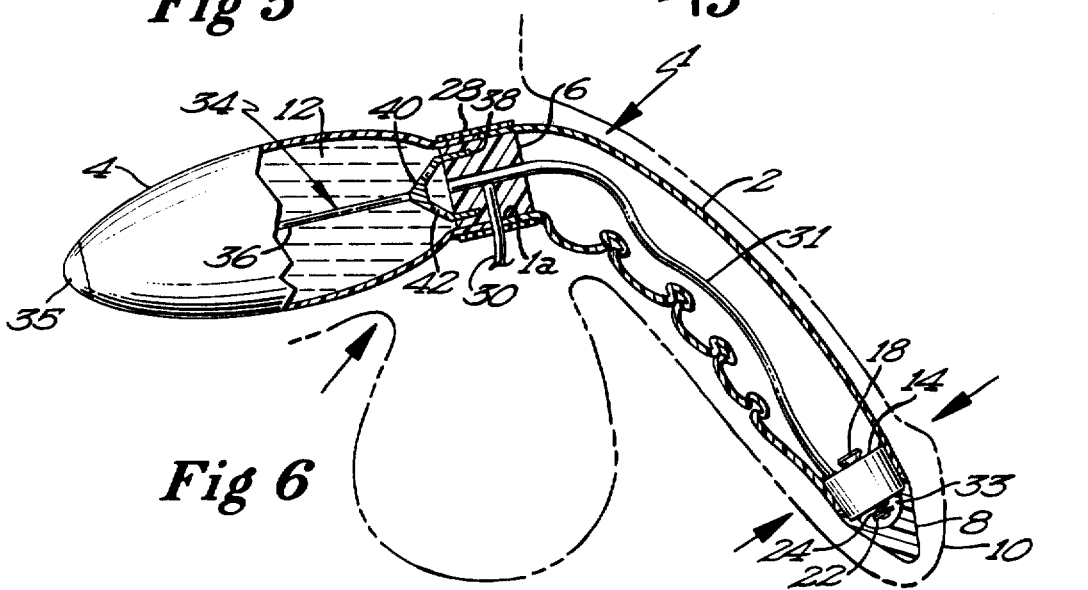
FIG. 6 is a side elevation view showing the penile prosthesis of FIG. 1 implanted in a male with the prosthesis in the flaccid state.

Also contained within the implant cylinder 1 is a valve section generally indicated by reference numeral 14 in FIGS. 2-4. Valve block 14 may also be made of polyurethane, or of hard rubber, such as medical grade silicone. In the embodiments shown herein, valve block 14 is positioned within distal end section 2 adjacent the outer or distal extremity thereof. Preferably, valve block 14 is positioned adjacent to the front tip 8 as shown for ease of location and manipulative accessibility. It is formed to include a valve seat 16 with which a valve poppet or element 18 cooperates to provide a fluid flow control function between reservoir chamber 12 and distal end section 2. Valve poppet 18 is connected by a stem 20 to a valve head 22. A coil spring 24 is positioned as shown between annular shoulder 26 of valve block 14 and valve head 22 so as to normally urge valve poppet 18 to the right as viewed in FIG. 2 in a closing position against seat 16. Valve block 14 is hollow internally so as to provide a chamber accommodating the aforesaid valve components.

The connecting block section 6 and the joint between cylinder sections 2 and 4 of the implant cylinder 1 are preferably reinforced and sealed by a band or ring 28 made of the same polyurethane or silicone material of which cylinder 1 is constructed. A charging tube 30 extends through reinforcing band 28 and the wall 1a of cylinder 1 surrounding connecting block 14 and connects with an internal fluid conduit 31. Tube 30 serves for initially charging fluid into cylinder 1 for containment within reservoir chamber 12 and distal end section 2. The fluid with which cylinder 1 is charged will be a biocompatible, preferably radiopaque liquid, such as a saline solution which is noncompressible. Fluid conduit 31 is preferably a polyurethane tube extending from reservoir chamber 12 through connecting block 6 and distal end section 2 to a point of connection with orifice 32 in valve block 14. Orifice 32 opens into space 33 between valve block 14 and distal tip 8.

A one piece stiffener generally indicated by reference numeral 34 is positioned within the walls of cylinder 1 defining proximal, root section 4 forming reservoir chamber 12. Stiffener 34 is preferably made from stainless steel and includes a rod 36 extending between a base-plug 35 and a continuous skirt head comprised of a conical segment 40 and a cylindrical skirt 38. Skirt 38 is imbedded within the rubber forming connecting block 6 and is apertured as shown for secure retention within the silicone rubber from which block 6 preferably is molded. The opposite end of stiffener 34 bears against the extreme, proximal end of the root section 4 of implant cylinder 1 through base plug 35. Apertures 42 formed in the conical segment 40 of stiffener 34 permit unimpeded fluid flow from reservoir chamber 12 into conduit 31 and thence into distal end section 2 through end space 33 and valve seat or port 16. Stiffener 34 supports the flexible walls forming the proximal, reservoir portion 4 of cylinder 1 at all times. The strength and rigidity which stiffener 34 lends to proximal section 4 of the implant device particularly aids in the insertion of proximal section 4 within the root end of the corpora cavernosa of a male patient at the location shown in FIG. 6.

In the embodiment of the penile prosthesis shown in FIGS. 1-6, the proximal root section 4 of the implant cylinder 1 which serves as reservoir chamber 12 also functions as the pump means. The walls of cylinder 1 defining proximal section 4 are resiliently compressible inwardly. Thus, the application of external pressure to proximal section 4 will cause fluid to be expelled therefrom under pressure into distal section 2 through conduit 31 and valve 16-18.

As noted above, cylinder 1 is adapted to be surgically implanted within the corpus cavernosum of the penis. Although one implant cylinder 1 could be satisfactorily utilized, it is anticipated that two separate prosthetic implant cylinders 1 will be utilized, with one of such cylinders being implanted within each of the corpus cavernosum of the penis in the manner shown in FIG. 6. Such a double cylinder prosthetic system provides a measure of redundency in case one cylinder should fail. The surgical procedure for implanting two of the cylinders 1 within the corpora cavernosa is substantially the same as that described in U.S. Pat. No. 3,954,102 with respect to the inflatable, prosthetic cylinders. Cylinders 1 are inserted into the corpora cavernosa through an incision made at the base of the penis. The corpora cavernosa regions of the penis are first dilated, as by the insertion of a metal rod through the incision to displace the erectile tissue and create a space for the subsequent insertion of the prosthetic cylinders 1. After insertion, distal end section 2 will extend within the pendulous portion of the penis, and proximal section 4 of the cylinder will extend into the root end of the corpora cavernosa as shown in FIG. 6. Proximal section 4 comprising the combined fluid reservoir and pump will be located within the root end of the corpora cavernosa at the location where it may be subjected to compression and pumping action by the application of manual pressure to the patient's perineal tissue.

The arrow in FIG. 6 indicates the location and direction of the application of manual pressure to the perineum for compressing the walls of pump-reservoir section 4 of cylinder 1. Such a pressing action will force fluid under pressure from proximal, reservoir section 4 through fluid conduit 31 and distal end space 33 against valve poppet 18, thereby overcoming the pressure of spring 24 and displacing valve poppet 18 to an open position with respect to seat 16. Pressurized fluid is thus caused to flow from reservoir 12 into distal end section 2. The resultant rigidizing of distal section 2 under fluid pressure produces an erection. When it is desired to return the penis to a flaccid state, it is only necessary for the patient to apply pressure to valve section 14 of the implant device. This may be done by utilizing the thumb and forefinger to apply squeezing pressure to the tissue just rearwardly of the glans penis as shown by the directional arrows in FIGS. 2, 5, and 6. The resultant squeezing action at the valve location will cause valve seat 16 to be compressed in one direction and elongated in the opposite direction as shown in FIG. 5. FIG. 3 illustrates the condition of the valve assembly in its normal, rest condition free from the application of any such squeezing pressure. The vertical deformation of valve seat 16 as illustrated in FIG. 5 results in the forming of openings 44 adjacent the top and bottom of valve poppet 18. Fluid flows from distal end section 2 of cylinder 1 through openings 44, space 33, and conduit 31 back into reservoir chamber 12, thereby depressurizing distal end section 2 and causing it to collapse to the condition shown in FIG. 6. This permits the penis to return to the flaccid or nonerect state of FIG. 6. The use of squeezing pressure to manipulate valve 16-18 to an open condition is substantially the same as that described for the bypass, squeeze valve in FIGS. 10-12 of U.S. Pat. No. 3,954,102. It is to be noted that valve block 14 is positioned along cylinder 1 at such a location near the distal tip that it will be located substantially as shown in FIG. 6 in immediate proximity to the glans penis where it will be readily locateable and accessible to squeezing pressure. With the valve positioned between the proximal and distal ends of the implant cylinder for ultimate location near the base of the penis upon implantation as disclosed in copending Application No. 264,202, critical measurements would possibly be required in order to insure proper placement of the implant cylinder in order to easily locate and operate the valve. Such critical placement considerations are eliminated by positioning the control valve adjacent the tip of the distal end of the cylinder as described above.

An alternative embodiment of the implantable penile prosthesis is shown in FIGS. 7-13. The implantable prosthetic cylinder 1 is substantially identical to that illustrated in FIGS. 1 and 2. Thus, the implantable prosthetic cylinder comprises a distal end section 2 which is pressurizable to assume a rigid condition, a proximal, root or rear section 4 which has flexible, resilient walls and serves as a fluid reservoir chamber 12 and as a pump device, and a connecting block 6 between proximal section 4 and distal section 2. Connector block 6 serves as a dividing wall between the two sections of the implant cylinder 1.

The embodiment of FIGS. 7-13 differs primarily in the utilization of a different type of check valve assembly than that shown and described as elements 14-16 in FIGS. 1-5. The check valve assembly is generally designated by reference numeral 46, and comprises a double check valve which must be manually actuated by external pressure to transfer fluid in either direction between reservoir chamber 4 and distal end section 2 for inflation and deflation of distal end 2. For this purpose, the double check valve 46 comprises a housing or chamber as shown in FIGS. 8-12 having resiliently flexible walls, preferably formed from medical grade rubber such as polyurethane. As may be noted most clearly by reference to FIGS. 9 and 10, deformable end walls 47 and 48 of valve housing 46 define a pair of spaced-apart valve seats 50 and 52 at opposite ends of the valve housing. A valve element in the form of a ball check member 54 is contained within the valve chamber 46 between the two seats. A fluid conduit 56 extends from the point of fluid flow communication with reservoir chamber 4 through connector block 6 and the interior of distal end section 2 to a point of connection with valve port 58 in seat 50. Fluid conduit 56 may also be made from the same medical grade rubber from which the prosthetic cylinder 1 is formed. A second, short conduit 60 extends from valve port 62 in the opposite wall 48 of valve housing 46, and may be connected at its free end, as by gluing, to attachment means comprising a stub protrusion 64 on front tip 8 of a cylinder 1. Thus, as with the valve block 14 of the preceding embodiment, valve assembly 46 is located adjacent to the tip or distal end extremity of distal end section 2 where it may be readily located and manipulated for selectively controlling fluid flow between reservoir chamber 4 and distal section 2 of the implant cylinder 1. Orifices 66 in conduit 60 open into the interior of distal section 2 of cylinder 1.

Figure 7:
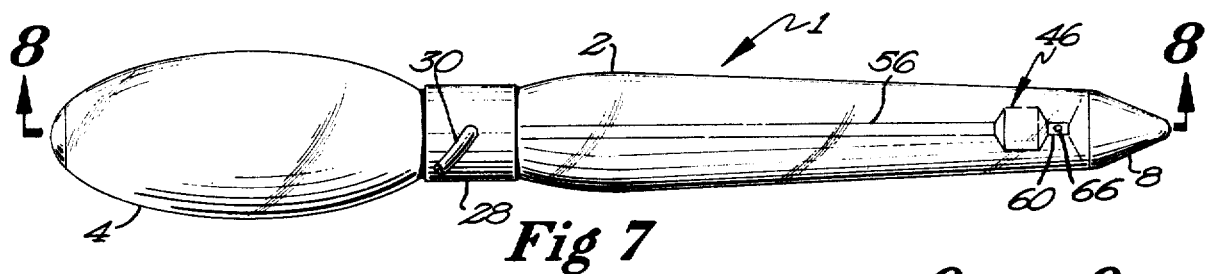
FIG. 7 is a side elevation view showing an alternative embodiment of the penile prosthesis as implanted in a male patient, with the prosthesis in an erect condition.
Figure 8:
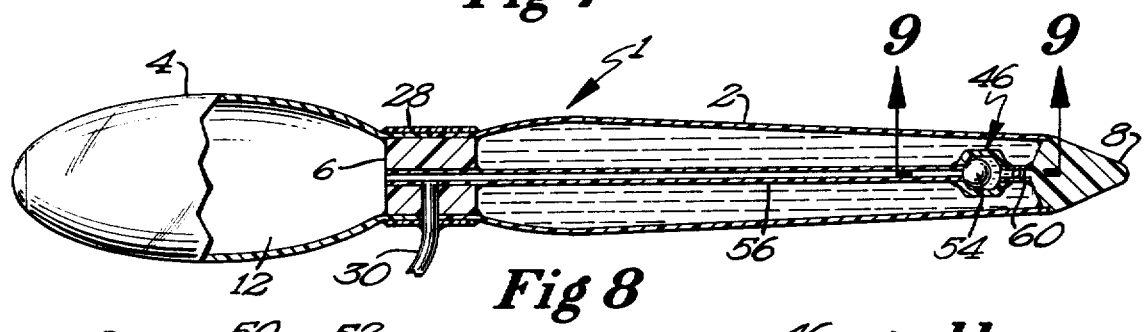
FIG. 8 is a section view showing the distal end and valve mechanism of the embodiment of the penile prosthesis depicted in FIG. 7.
Figure 9:
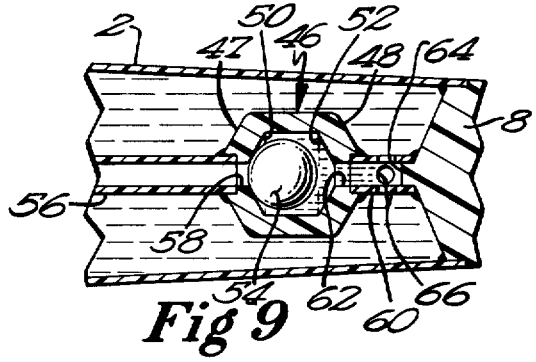
FIG. 9 is a fragmentary section view taken along lines 9—9 of FIG. 8 and showing the valve mechanism in the position wherein the distal, front end of the prosthesis is filled with fluid.
Figure 10:
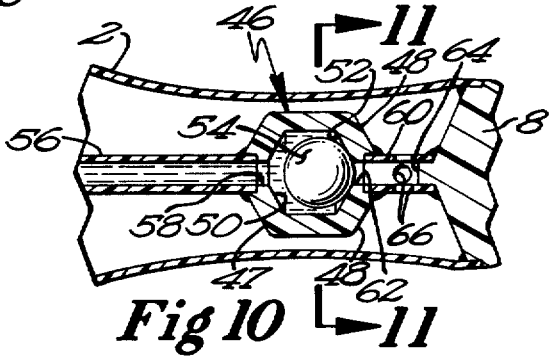
FIG. 10 also shows the same cross section view of the valve assembly as depicted in FIGS. 8 and 9, but with the valve assembly in the position which it will assume when the proximal, rear reservoir end of the prosthesis is filled with fluid.

Ball check member 54 will cooperate with valve seats 50 and 52 to normally block the flow of pressurized fluid in both directions between reservoir chamber 4 and distal section 2. When the rear reservoir chamber 4 is filled with fluid, ball check member 54 will be in a closing position against valve seat 62 as shown in FIG. 10. Thus, even if the fluid in reservoir chamber 4 should be inadvertently pressurized, as by the patient's sitting on the proximal, rear end section defining reservoir 12, the fluid under pressure passing through conduit 56 would urge ball check member 54 tightly against seat 62. Similarly, when the distal cylinder 2 is inflated for an erection as illustrated in FIGS. 7 and 8, the pressurized fluid therein will act on ball check member 54 to hold it tightly in closing relation to valve seat 50 as shown in FIG. 9. The fluid under pressure is thus alternately locked into either the rear reservoir chamber 12 or the distal end section 2 of cylinder 1.

Figure 11:
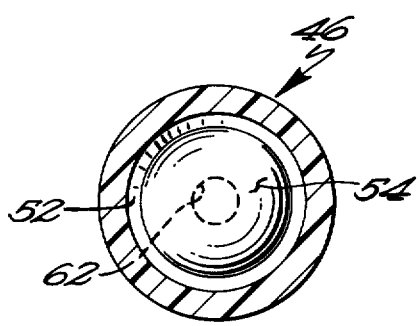
FIG. 11 is a section view of the valve mechanism taken along lines 11—11 of FIG. 10 with the valve closed.
Figure 12:
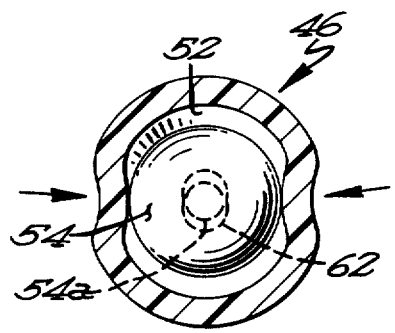
FIG. 12 is a section view taken at the same location on FIG. 10 as FIG. 11, but with the valve seat manually displaced to an open position.
Figure 13:
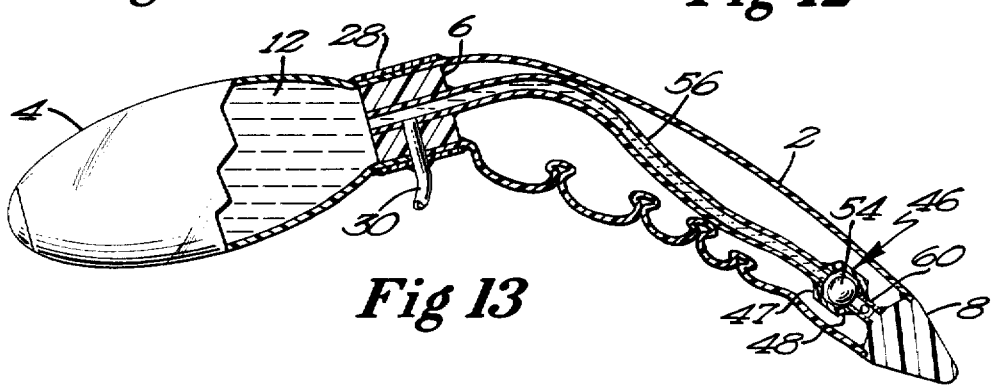
FIG. 13 is a side elevation, section view showing the penile prosthesis of FIG. 7 in the flaccid state with the fluid in the proximal, rear reservoir.

The application of squeezing pressure through the pendulous penis to the walls of distal section 2 as indicated in FIG. 10 is required to open either valve port 58 or valve port 62. FIG. 11 shows the ball check member 54 engaged with seat 52 to close valve port 62. Under the influence of squeezing pressure as indicated in FIGS. 10 and 12, valve port 62 will be deformed to an elongated shape. As a result, a flow passage will be opened at the elongated end extremities of port 62 which extend beyond the circular segment 54a of ball check member 54, which normally seats in conformity with port 62. With valve port 62 opened by such manipulative, squeezing action, the application of pressure through the perineum as shown by the directional arrow in FIG. 6 will cause fluid under pressure to flow through conduit 56, valve port 60, and orifices 66 of conduit 60 into the interior of distal section 2 for the pressurization and inflation thereof. When it is desired to return the penis to a flaccid state, the pendulous penis is again squeezed just rearwardly of the glans penis so as to again deform the flexible wall of valve chamber 46. This will cause valve port 58 to be deformed to an elongated shape the same as indicated above with respect to valve port 62. As a result a flow passage will be opened therethrough around ball check member 54, and fluid under pressure contained within distal section 2 will flow under the existing pressure differential through orifices 66, conduit 60, valve port 58, and conduit 56 into the rear reservoir chamber 12. This will return the prosthetic cylinder 1 to the flaccid state shown in FIG. 13. It is to be noted that the locking in of fluid in rear reservoir chamber 12 by means of the double check valve assembly 46 ensures that there will be an adequate supply of pressurizing fluid within chamber 12 to rigidize distal end section 2 when pumping on the flexible walls of proximal section 4 defining the rear reservoir chamber 12.

FIGS. 14 through 21 illustrate still another embodiment of the invention wherein a separate, elastomeric bulb 68 is employed as a pump device rather than using a flexible walled proximal section 4 of cylinder 1 as a pumping means. Bulb 68 is sized to fit conveniently within the scrotal sac of the patient as illustrated in FIG. 14, and is connected to a combined valve block and connecting section 70 by means of a length of elastomeric tubing 74. As with the embodiment of FIG. 1, valve block and connector section 70 may be reinforced by a band or ring 72 made of the same silicone or polyurethane material of which cylinder 1 is constructed. Cylinder 1 is of the same basic construction as described above with respect to FIGS. 1 and 2, and is comprised of a distal section 2 and a proximal, root section 4 which serves as a fluid reservoir chamber 12. It is to be noted that a stiffener of the same shape and construction as illustrated and described above with respect to FIG. 1 may be utilized in the embodiments of FIGS. 7 through 13 and 14 through 21 to lend longitudinal rigidity and strength to proximal, rear reservoir section 4 of implant cylinder 1.

Valve block 70 is constructed and assembled to allow fluid to flow from reservoir chamber 12 of proximal section 4 of the implant cylinder to distal section 2 only when pump bulb 68 is squeezed. To this end, valve assembly 70 is comprised of a central, cylindrical core 76 which is press fitted into a surrounding sleeve 78, as illustrated in FIGS. 20-21. Valve assembly components 76 and 78 are formed from rubber, such as medical grade silicone, and are joined at one end by adhesive material 80. Otherwise, these two valve components are free to move with respect to each other. An annular groove 82 formed in the front face of valve sleeve 78 defines a flap valve 84 which normally seats against the adjacent surface of valve core 76, and provides a check valve function as hereinafter set forth.

Cylindrical core 76 of the valve assembly is formed to provide a central valve chamber 86 formed in one end to provide a valve seat 88 into which inlet port 90 opens. A valve element in the form of a ball check member 92 is contained within valve chamber 86 for closing engagement with seat 88 over port 90. Square corner elements 94 are formed on the walls of valve chamber 86 opposite from valve seat 88 so as to ensure that an open flow passage is always provided on this side of ball check member 92 into valve chamber 86. At least one orifice 96 extends through the wall of central valve core 76 to the line of contact between cylindrical core 76 and surrounding sleeve 78. Another annular groove or cavity 98 is formed in the rear end of valve sleeve 78 to provide a membrane 100 in overlying, closing relation to valve port 96. Connecting tube 74 opens into valve chamber 86 and places scrotal pump 68 in fluid flow communication therewith. It is to be noted that since reservoir chamber 12 for the pressurizing fluid is formed within proximal section 4 of the implant cylinder, pump bulb 68 need only function as a fluid transfer pump, and not as a reservoir chamber. Accordingly, pump bulb 68 is of relatively small size and may be implanted within the scrotal sac as shown in FIG. 14 without unduly interfering with bodily organs contained therein or causing discomfort to the patient.

A passageway 102 extends as a through hole all of the way through valve sleeve 78, and serves as a flow passage connecting reservoir chamber 12 with a fluid conduit 104. Conduit 104 extends through the interior of distal section 2 to the front end thereof where it is attached to one end of a double check valve assembly generally indicated by reference numeral 106.

Check valve assembly 106 is of the same type disclosed above with respect to FIGS. 7-12, but represents a preferred embodiment thereof. It is to be noted that the double check valve embodiment 106 may be utilized in place of check valve unit 46 of FIGS. 7-12. Valve assembly 106 is comprised of an elongated, elastomeric valve body 108 of generally cylindrical configuration. Silicone or polyurethane may be used to form valve body 108. A central valve housing segment 110 of circular cross section is formed along the length of elongated valve body 108 and is separated from a pair of enlarged diameter end collars 112 and 114 by reduced diameter tubular segments 116 and 118. These tubular segments define a central flow passage 117. Both end collars 112 and 114 are scalloped to provide lobes 120 and 122, respectively, as shown in FIG. 16. The outer diameter of these lobes is sized to slightly clear the adjacent wall surface of tapered distal segment 2 of implant cylinder 1 as shown in FIG. 15, whereby the entire valve body 108 may be positioned relatively snugly within the tapered distal end 2 of the cylinder 1. Circumferentially spaced lobes 112 and 114 permit the flow of pressurizing fluid therebetween along the length of distal segment 2. The placement of radially projecting central valve housing segment 110 between reduced diameter tubular segments 116 and 118 permits it to be easily located for squeezing deformation when actuating the double check valve unit. As in the case of the double-acting check valve unit 46 of FIGS. 7-12, this is accomplished by applying squeezing pressure in the direction indicated by the arrows in FIG. 19 to the pendulous penis just rearwardly of the glans penis to deform the elastomeric valve housing segment 110 inwardly as shown in FIGS. 18 and 19.

Central valve cavity 124 within valve housing segment 110 contains a ball check member 126 sized and positioned to normally seat in closing relationship to a pair of opposed valve seats 128 and 130. External manipulation of the valve assembly 106 is required to open valve seats 128 and 130 to permit flow through internal flow passage 117 for both inflation and deflation of distal end segment 2 of cylinder 1. This is accomplished as set forth above by applying squeezing pressure in the direction of the arrows in FIG. 19 to the pendulous penis adjacent to central valve housing segment 110. When this is done, the central valve housing 110 will be flattened as shown in FIGS. 18 and 19 to thereby elongate valve seats 128 and 130. As a result, clearance passages 132 will be formed between spherical ball check member 126 and valve seats 128 and 130. Both valve seats will always be opened simultaneously in this manner to permit fluid flow through flow passage 117 and fluid conduit 104.

In operation, pumping action is applied to bulb 68 by repetitive, squeezing manipulation thereof through the scrotal sac, when the patient desires to achieve an erection. As the walls of pump bulb 68 are released outwardly on the suction stroke of each pumping manipulation, ball check valve element 92 is drawn to the right as viewed in FIG. 20 to open valve seat 88 and inlet port 90. On this suction stroke, fluid is thus drawn from reservoir chamber 12 through port 90 and valve chamber 86 into pump bulb 68 through tube 74. As the pump bulb is sequentially squeezed on the pumping stroke as illustrated in FIG. 22, fluid is expelled under pressure from bulb 68 through tube 74 into valve chamber 86. This has the effect of forcing ball check member 92 to the left into closing engagement with seat 88 as shown in FIG. 22. Fluid under pressure will pass from valve chamber 86 through port 96 between the inner peripheral surface of valve sleeve 78 and the adjacent, outer peripheral surface of cylindrical valve core 76. The pressurized fluid will force flap valve 84 outwardly away from the adjacent surface of valve core 76 to the open position shown in FIG. 22. Fluid will thus be discharged under pressure into the interior of distal section 2 of implant cylinder 1. This causes flexible distal section 2 to expand and rigidize as shown in FIG. 14, thereby producing an erection. Pressurized fluid within distal section 2 will act on the top surface of flap valve 84 to hold it in tight, sealing contact with the outer surface of valve core 76. In this manner, flap valve 84 performs a checking function to assist in holding the pressurized fluid within distal end 2.

When it is desired to return the penis to a flaccid state, valve housing 110 of double check valve 106 is squeezed inwardly as described above with respect to FIGS. 18 and 19 by applying squeezing pressure to the pendulous penis just rearwardly of the glans penis. This elongates the valve seats 128 and 130 to provide the open flow passage 132 around ball check member 126. As a result, the pressure differential permits the relatively high pressure fluid within distal section 2 to flow through valve passage 117, fluid conduit 104, and passage 102 within valve sleeve 78 back into reservoir chamber 12 within proximal end section 4 of the implant cylinder. The shape of the central cavity 124 of valve 106 as shown in FIG. 15 is significant in that it contains the ball check member 126 in tight, closing engagement with both of the opposed valve seats 128 and 130. This is accomplished by forming the central cavity 124 as an annular chamber much narrower than the diameter of ball check member 126. A relatively minimal amount of squeezing pressure is required for activation of valve 106 to the open position shown in FIGS. 18 and 19, and a large force can be applied without closing off the valve.

Even if the fluid within reservoir chamber 12 should be inadvertently pressurized, as by sitting on the rear, proximal reservoir end 4 of implant cylinder 1, pressurized fluid cannot flow into distal end section 2. This lock-in feature is provided by annular membrane 100. Pressurized fluid within reservoir chamber 12 will enter annular cavity 98 and act on the surface of membrane 100. This provides an offsetting pressure to that generated within valve chamber 86 and orifice 96, with ball check valve 92 having been displaced to an open position by the pressurized fluid within chamber 12. Thus, membrane 100 will be held in sealing engagement across orifice 96 to prevent flow therethrough into distal end section 2. Undesired flow of pressurized liquid from reservoir chamber 12 through valve flow passage 102 and conduit 104 into distal end section 2 is provided by normally closed ball check member 126 of valve assembly 106.

As stated above, distal end section 2 of the implant cylinder 1 is made of flexible, medical grade material which will permit it to collapse and bend to the condition shown in FIG. 6. Distal end section 2 is also inflatable to the extent that it may be rigidized in a straight condition for producing an erection as illustrated in FIG. 7. The term "inflatable" as used herein is intended to mean a penile prosthesis of the type having a distal end section 2 which is flexibly bendable to permit the penis to assume a flaccid state, but which rigidizes upon being pressurized to produce an erection. The implant cylinder as disclosed herein may be made of silicone or polyurethane so that distal end section 2 is expandable in girth and length, or it may be made of materials which permit distal end section 2 to distend only to a limited extent. The latter type of cylinder has the advantage that it can be rigidized with a lesser volume of fluid. Such a limited distensible cylinder can be made of silicone or polyurethane reinforced by nonstretching fibers such as Dacron. The fiber reinforcing limits the ability of distal section 2 to distend.

It will readily be appreciated that the implantable prosthetic cylinder as disclosed herein with its self-contained fluid reservoir chamber at one end thereof will greatly simplify surgical implant procedures. No separate, reservoir chamber containing fluid is required to be implanted within the patient at a location remote from the penis. The embodiments illustrated and described with respect to FIGS. 1–6 and 7–13 also eliminate the need for a separate pump bulb by utilizing the proximal reservoir chamber section of the implant cylinder as the pumping device. With respect to the embodiment of FIGS. 7–13, the double check valve 46 must be manually squeezed to an open position simultaneously with the application of pumping pressure to reservoir pump 4 through the perineum in order that pressurized fluid may flow into the distal end 2 of the implant cylinder. If two cylinders are implanted, one in each corpora cavernosum as would normally be the case, each cylinder will be filled and pressurized separately. In most cases the two cylinders can be deflated simultaneously by the application of squeezing pressure to the pendulous penis at the check valve location. With respect to the embodiment of FIGS. 14–22, the utilization of a fluid reservoir chamber formed within the implant cylinder, and the embodiment of the valve mechanisms within the implant cylinder itself, permits the separate pump bulb implanted within the scrotal sac to be of relatively small size.

It is anticipated that various changes may be made in the construction, shape and operation of the penile prosthetic devices as disclosed herein without departing from the spirit and scope of the invention as defined by the following claims.

What is claimed is:

1. An implantable penile prosthesis comprising:
at least one elongated cylinder adapted to be implanted within a patient's penis, said cylinder having a flexible distal end section for implantation within the pendulous penis which is constructed to rigidize upon being filled with pressurizing fluid, and a proximal, rear end section adapted to be implanted within the root end of the penis;
a fluid reservoir chamber formed within said proximal, rear end section of said cylinder;
pump means manually operable to transfer fluid under pressure from said fluid reservoir chamber to said flexible distal end of said cylinder for achieving an erection; and
externally operable valve means contained within said cylinder for controlling the flow of fluid back and forth between said fluid reservoir chamber and said flexible distal end of said cylinder, said valve means being located within said flexible, distal end section of said cylinder at a position where it will be readily accessible within the pendulous penis for actuation at a distally remote location from the root end thereof, and said valve means incorporating check valve means normally precluding the flow of pressurized fluid from within said flexible distal end section of said cylinder through said valve means back to said fluid reservoir chamber; and
fluid conduit means within said elongated cylinder in fluid flow communication between said fluid reservoir chamber and said valve means.

2. An implantable penile prosthesis as defined in claim 1 wherein:
said valve means is located adjacent to the distal end extremity of said flexible distal end section of said elongated cylinder at a position where it will be disposed in immediate proximity to the glans penis, rearwardly thereof, when said penile prosthesis is implanted within a patient's penis.

3. An implantable penile prosthesis as defined in claim 1 wherein:
said valve means is comprised of a valve element and a seat constructed and assembled in cooperative juxtaposition to each other in such a way that said valve element is displaced to an open position by pressurized fluid delivered under pressure from said fluid reservoir chamber by said pump means, to thereby permit pressurized fluid to flow into said distal end section of said cylinder for penile erection.

4. An implantable penile prosthesis as defined in claim 3 wherein:
said valve seat is deformable by means of external manipulation through squeezing pressure applied to the pendulous penis to open a flow passage through said seat and around said valve element to permit the return flow of fluid from said distal end section of said cylinder to said reservoir chamber for returning the penis to a flaccid state.

5. An implantable penile prosthesis as defined in claim 1 wherein:
said valve means is comprised of a plurality of valve seats assembled in cooperative juxtaposition with valve element means so as to serve as said check valve means, normally blocking the flow of pressurized fluid in both directions through said fluid conduit means between said fluid reservoir chamber and said distal end section of said cylinder, whereby said valve means must be externally actuated to either inflate or deflate said distal end section of said cylinder.

6. An implantable penile prosthesis as defined in claim 5 wherein:
said valve seats are deformable by means of external manipulation through the application of pressure to the pendulous penis to open flow passages through said valve seats and around said valve element means to permit the flow of fluid in either direction between said fluid reservoir chamber and said distal end section of said cylinder.

7. An implantable penile prosthesis as defined in claim 6 wherein:
said valve means comprises a chamber with deformable walls defining said valve seats at spaced apart locations with respect to each other, and said valve element means comprises a check valve member contained within said chamber and movable back and forth under fluid pressure to alternate closing positions against said valve seats to block the flow of pressurized fluid in both directions between said fluid reservoir chamber and said distal end section of said cylinder.

8. An implantable penile prosthesis as defined in claim 7 wherein:
said valve means is located adjacent to the distal end extremity of said flexible distal end section of said elongated cylinder at a position where it will be disposed in immediate proximity to the glans penis, rearwardly thereof, when said penile prosthesis is implanted within a patient's penis; and
said fluid conduit means comprises a first conduit extending from said reservoir chamber into said distal end section of said cylinder to a point of fluid flow connection to one side of said valve chamber having deformable walls at a first valve seat location, and a second conduit extending from the opposite side of said valve chamber at a second valve seat location, and orifice means in said second conduit opening into said distal end section of said cylinder.

9. An implantable penile prosthesis as defined in claim 8 wherein:
said second conduit extends between said valve chamber and attachment means to which it is mounted on the distal end extremity of said flexible, distal end section, and said first conduit is mounted at one end thereof in divider wall means positioned between adjacent ends of said reservoir chamber and said distal end section of said cylinder, whereby said fluid conduit means is supported between said divider wall means and said attachment means.

10. An implantable penile prosthesis comprising:
at least one elongated cylinder adapted to be implanted within a patient's penis; said cylinder having a flexible distal end section for implantation within the pendulous penis which is constructed to rigidize upon being filled with pressurizing fluid, and a proximal, rear end section adapted to be implanted within the root end of the penis;
a fluid reservoir chamber formed within said proximal, rear end section of said cylinder;
pump means manually operable to transfer fluid under pressure from said fluid reservoir chamber to said flexible distal end of said cylinder for achieving an erection; and
externally operable valve means contained within said cylinder for controlling the flow of fluid back and forth between said fluid reservoir chamber and said flexible distal end of said cylinder, said valve means being comprised of a plurality of valve seats positioned in cooperative juxtaposition with valve element means so as to serve as check valve means normally blocking the flow of pressurized fluid in both directions through said fluid conduit means between said fluid reservoir chamber and said distal end section of said cylinder, whereby said valve means must be externally actuated to either inflate or deflate said distal end section of said cylinder; and
fluid conduit means within said elongated cylinder in fluid flow communication between said fluid reservoir chamber and said valve means.

11. An implantable penile prosthesis as defined in claim 10 wherein:
said valve means is manually operable by the application of external pressure thereto and is located within said flexible, distal end section of said cylinder at a position where it will be readily accessible for manual manipulation by the application of pressure to the pendulous penis at a distally remote location from the root end thereof.

12. An implantable penile prosthesis as defined in claim 11 wherein:
said valve means is located adjacent to the distal end extremity of said flexible distal end section of said elongated cylinder at a position where it will be disposed in immediate proximity to the glans penis, rearwardly thereof, when said penile prosthesis is implanted within a patient's penis.

13. An implantable penile prosthesis as defined in claim 10 wherein:
said valve means comprises a housing of flexible, elastomeric material defining said valve seats and said valve element means comprises a single check member normally contained within said housing in closing contact with both of said valve seats, said valve seats being deformable by the application of external pressure to open flow passages through said valve seats and around said valve check member to permit the flow of fluid in either direction between said fluid reservoir chamber and said distal end section of said cylinder.

14. An implantable penile prosthesis as defined in claim 13 wherein:
said valve means is located within said flexible, distal end section of said cylinder at a position where said flexible housing will be readily accessible for manual manipulation by the application of squeezing pressure to the pendulous penis at a distally remote location from the root end thereof.

15. An implantable penile prosthesis as defined in claim 13 wherein:
said valve means comprises an elongated valve body having a pair of end collars joined by tubular segments of reduced diameter in comparison with that of said end collars, and said flexible valve housing is formed along the length of said elongated valve body with an annular shape between said end collars for ease of location and squeezing deformation.

16. An implantable penile prosthesis comprising:
at least one elongated cylinder adapted to be implanted within a patient's penis, said cylinder having a flexible distal end section for implantation within the pendulous penis which is constructed to rigidize upon being filled with pressurizing fluid, and a proximal, rear end section adapted to be implanted within the root end of the penis;
a fluid reservoir chamber formed within said proximal, rear end section of said cylinder;
fluid conduit means within said elongated cylinder in fluid flow communication between said fluid reservoir chamber and said distal end section;
externally operable valve means contained within said cylinder for controlling the return flow of the fluid from said distal end section to said reservoir chamber through said fluid conduit means, said valve means incorporating check valve means normally precluding the flow of pressurized fluid from within said distal end section of said cylinder through said fluid conduit means back to said fluid reservoir chamber; and pump means comprising an elastomeric bulb adapted to be implanted within the male scrotum, said pump bulb being in fluid flow communication with said fluid reservoir chamber and with said distal end section through a valve assembly positioned within said cylinder between said chamber and distal end section, said valve assembly including a check valve between said reservoir chamber and said pump bulb for permitting flow in only one direction from said reservoir chamber into said pump bulb.

17. An implantable penile prosthesis as defined in claim 16 wherein:

said valve assembly includes a second check valve between said pump bulb and said distal end section of said cylinder for permitting fluid flow in only one direction on the pumping stroke of said bulb from said bulb into said distal end section.

18. An implantable penile prosthesis as defined in claim 17 wherein:

said valve assembly comprises a central core and an elastomeric sleeve in surrounding relation thereto, said central core having orifice means connecting the outlet of said pump bulb with the surface contact zone between said sleeve and said valve core; and flap valve means formed in said valve sleeve and positioned to normally contact the adjacent surface of said valve core in sealing contact therewith, whereby pressurized fluid flowing from said pump bulp on the pumping stroke thereof through said orifice means will force said flap valve away from said valve core to an open position to permit pressurized fluid to discharge into said distal end section of said implant cylinder.

19. An implantable penile prosthesis as defined in claim 18 wherein:

an annular cavity is formed in said valve sleeve in fluid flow communication with said fluid reservoir chamber to define a flexible membrane in overlying relation to said orifice means, whereby the inadvertent pressurization of said fluid reservoir chamber of said proximal section of said cylinder will result in a balanced pressure on both sides of said membrane with pressurized fluid flow through said first check valve into said orifice means, thereby maintaining said membrane in sealing relation to said orifice means to prevent the inadvertent pressurization of said distal end section of said cylinder.

20. An implantable penile prosthesis as defined in claim 16 wherein:

said valve means is manually operable by the application of external pressure, and is located within said flexible, distal end section of said cylinder at a position where it will be readily accessible for manual, squeezing manipulation by the application of pressure to the pendulous penis at a distally remote location from the root end thereof, and said valve means is comprised of a plurality of valve seats positioned in cooperative juxtaposition with valve element means so as to serve as check valve means normally blocking the flow of pressurized fluid in both directions through said fluid conduit means between said fluid reservoir chamber and said distal end section of said cylinder.

21. An implantable penile prosthesis as defined in claim 20 wherein:

said fluid conduit means comprises a flow passage extending through said valve assembly between said reservoir chamber and the interior of said distal end section, and a fluid conduit connected between said fluid passage and said manually operable valve means.

* * * * *